United States Patent [19]

Ishikawa et al.

[11] Patent Number: 4,678,297
[45] Date of Patent: Jul. 7, 1987

[54] OPHTHALMIC INSTRUMENT

[75] Inventors: Yasuyuki Ishikawa, Kawaguchi; Isao Matsumura, Yokosuka, both of Japan

[73] Assignee: Canon Kabushiki Kaisha, Tokyo, Japan

[21] Appl. No.: 851,861

[22] Filed: Apr. 10, 1986

Related U.S. Application Data

[63] Continuation of Ser. No. 555,528, Nov. 28, 1983, abandoned.

[30] Foreign Application Priority Data

Nov. 30, 1982 [JP] Japan .................................. 57-210937

[51] Int. Cl.$^4$ .......................... A61B 3/14; A61B 3/10
[52] U.S. Cl. .................................... 351/208; 351/211; 354/62
[58] Field of Search ....................... 351/206, 208, 211; 354/62

[56] References Cited

U.S. PATENT DOCUMENTS

| | | | |
|---|---|---|---|
| 4,357,079 | 11/1982 | Karasawa | 351/208 |
| 4,365,872 | 12/1982 | Nunokawa | 351/208 |
| 4,436,389 | 3/1984 | Sano | 351/208 |
| 4,453,808 | 6/1984 | Takahashi et al. | 351/208 |
| 4,511,227 | 4/1985 | Nunokawa et al. | 351/208 |

Primary Examiner—Rodney B. Bovernick
Attorney, Agent, or Firm—Fitzpatrick, Cella, Harper & Scinto

[57] ABSTRACT

An ophthalmic instrument for effecting eye measurement with an eye-measuring target mark projected onto an eye to be examined, includes a photodetector provided at a position optically conjugate with the position of the corneal reflection image of the eye-measuring target mark to thereby determine the quality of the accuracy of alignment with the eye to be examined.

10 Claims, 11 Drawing Figures

OPHTHALMIC INSTRUMENT

This application is a continuation of application Ser. No. 555,528 filed Nov. 28, 1983, now abandoned.

BACKGROUND OF THE INVENTION

1. Field of the Invention

This invention relates to an apparatus for determining the alignment accuracy of an ophthalmic instrument, and in particular to an apparatus capable of determining the accuracy of alignment between a pre-aligned eye to be examined and ophthalmic instrument and further effecting fine adjustment of the alignment.

2. Description of the Prior Art

When a light flux is to be projected onto an eye to be examined to thereby measure the refractive power or the like of the eye, unless alignment of the ophthalmic instrument and the eye to be examined is accurately effected, a measurement error may not only occur but it also may not be possible to obtain a photograph for use as a determination material when it is desired to effect determination of characteristics of the eye with a photograph or the like. Therefore, in an ophthalmic instrument, for example, a target mark for alignment is projected onto the eye to be examined, a corneal-reflection image (virtual image) formed by corneal reflection is caused to be imaged in a television camera while, at the same time, a target mark fixed to the ophthalmic instrument is caused to be imaged on the same picture plane, and the two images are made coincident with each other, thereby accomplishing alignment.

However, when the eye to be examined is continually moving, an error may sometimes occur to the measurement value due to displacement resulting from a time delay until the measurement is made even if alignment is effected.

SUMMARY OF THE INVENTION

It is an object of the present invention to provide an apparatus which is capable of discriminating the quality of the accuracy of alignment with the eye to be examined during measurement of the eye.

It is a further object of the present invention to provide an ophthalmic instrument in which a target mark for eye measurement functions also as a target mark for determining the quality of the accuracy of alignment with the eye to be examined.

It is a still a further object of the present invention to provide an apparatus in which a line sensor such as a CCD or a photodiode is used as a photodetector and the quality of the accuracy of alignment with the eye to be examined in horizontal, vertical and longitudinal directions is automatically discriminated.

The present invention will become fully apparent from the following detailed description thereof taken in conjunction with the accompanying drawings.

DESCRIPTION OF THE PREFERRED EMBODIMENTS

Figure 1:
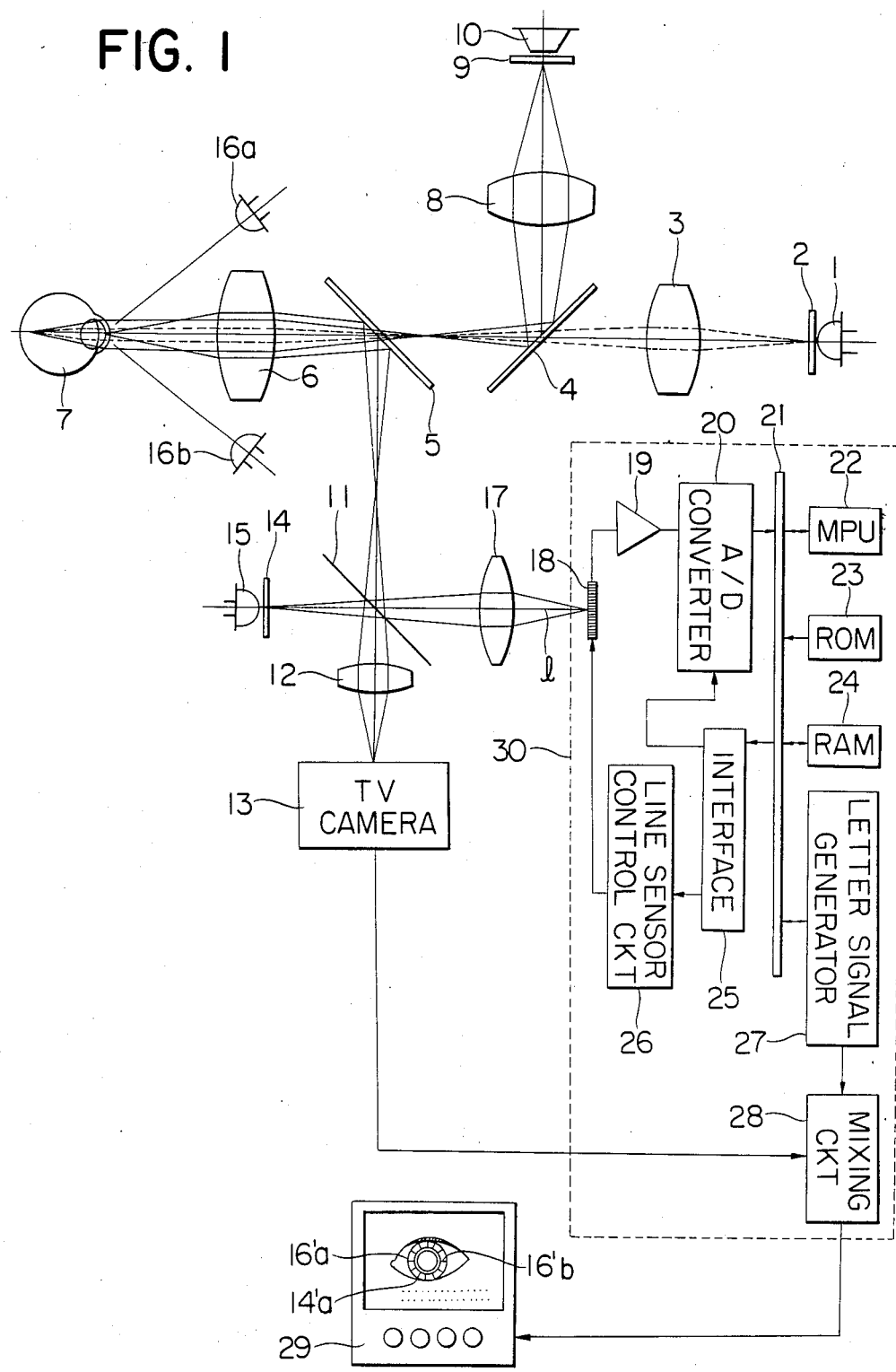
FIG. 1 is a view of the construction of an optical system and a control circuit showing an embodiment of the present invention.

As shown in FIG. 1, a light from a measuring projection chart 2 illuminated by a light source 1 is projected onto the fundus of an eye 7 to be examined through a lens 3, beam splitters 4, 5 and an objective lens 6. The light reflected from the fundus of the eye is transmitted through the objective lens 6 and the beam splitter 5 and is reflected by the beam splitter 4, whereafter it is detected by a light receiver 10 via a lens 8 and a light-receiving mask 9. The refractive power of the eye is found on the basis of the light detected by the receiver.

Figure 2:
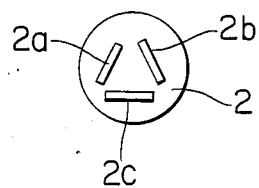
FIGS. 2 and 3 are plan views of projection charts for eye measurement and alignment, respectively.
Figure 4:
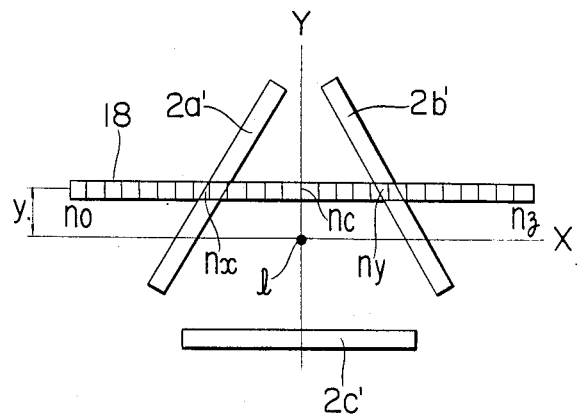
FIGS. 4, 5 and 6 are plan views showing the positional relation between a line sensor and the corneal reflection images of the projection chart.

On the other hand, of the light from the chart 2, the light flux reflected by the cornea of the eye 7 to be examined passes through the objective lens 6 and is reflected by the beam splitter 5, whereafter it is reflected by a beam splitter 11 and projected by a lens 17 onto a light-receiving element, for example, a line sensor 18 such as a CCD. The light-receiving element 18 is rendered optically conjugate with the corneal reflection image position by the objective lens 6 and the lens 17. If the projection chart is a slit having openings in three directions as shown in FIG. 2 and the line sensor 18 is disposed relative to corneal reflection images 2a' and 2b' as shown in FIG. 4, vertical and horizontal deviations of alignment are detected from the positional relation between the two images 2a' and 2b' on the line sensor and longitudinal deviation of alignment is detected from blur.

Figure 3:
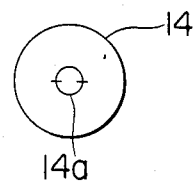

Now, the standard for the alignment operation is as follows: the front portion of the eye to be examined is illuminated by light sources 16a and 16b and projected onto the light-receiving surface of a television camera 13 by the use of the objective lens 6 and relay lens 12. Simultaneously therewith, the image 14a' of the target mark 14a of a chart 14 shown in FIG. 3 which is illuminated by a light source 15 is made coincident with the corneal reflection images 16'a and 16'b of light sources 16a and 16b for illuminating the front eye portion, whereby the vertical and horizontal positions are adjusted and the longitudinal position is adjusted so that the corneal reflection images 16'a and 16'b are formed with smallest size. That is, the alignment accuracy obtained by effecting pre-alignment by this means is discriminated by the use of the present invention.

The positional relation between the line sensor 18 and the corneal reflection images 2a' and 2b' of the slits of the chart 2 will now be described in detail by reference to FIG. 4. This Figure shows the state when the eye to be examined and the apparatus according to the present invention have been properly aligned. In FIG. 4, l designates the optic axis of the optical system of the present apparatus and, when proper alignment has been achieved, the corneal reflection images 2a', 2b' and 2c' are in a point-symmetrical relation about the optic axis 1. The line sensor 18 is disposed at a position deviated by y from the X-axis so that it is equal in horizontal measure relative to the XY coordinates having 1 as their origin and that in the vertical relation, it crosses the vicinity of the centers of the corneal reflection images 2a' and 2b'. Of course, detection of any alignment deviation would also be possible with an arrangement other than that shown in FIG. 4, but the arrangement of this Figure is more advantageous in respect of signal processing, detection range, etc. Further, it is desirable that the center $n_c$ of the line sensor be properly disposed relative to the Y-axis, but the interval per 1 bit of the line sensor is narrow and therefore, the center of the line sensor is sometimes not properly disposed. In such cases, the amount of deviation may be pre-measured and input by a digital switch or the like for correction.

Figure 7:
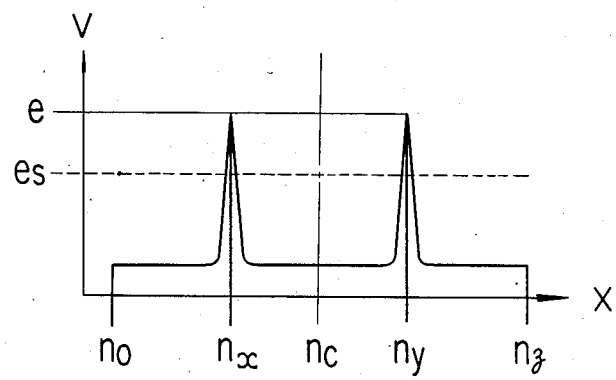
FIGS. 7 and 8 show the output waveforms when the line sensor is and is not aligned in the direction of the optic axis.

Now, assuming that the line sensor 18 is divided into $n_o$ to $n_z$, for example, 256 bits, the image 2a' is formed at an address $n_x$ and the imge 2b' is formed at an address $n_y$. The output in this state is shown in FIG. 7. The waveform is formed by two pointed crests having their peaks respectively at the address $n_x$ and the address $n_y$, and the peak level thereof is e. The addresses $n_x$ and $n_y$ are symmetrical relative to the center $n_c$ and thus, $n_c - n_x = n_y - n_c$ and the interval $d = n_y - n_x$ between $n_x$ and $n_y$ is of a predetermined width. This width d is pre-stored as a reference value in a ROM to be described later.

Figure 5:
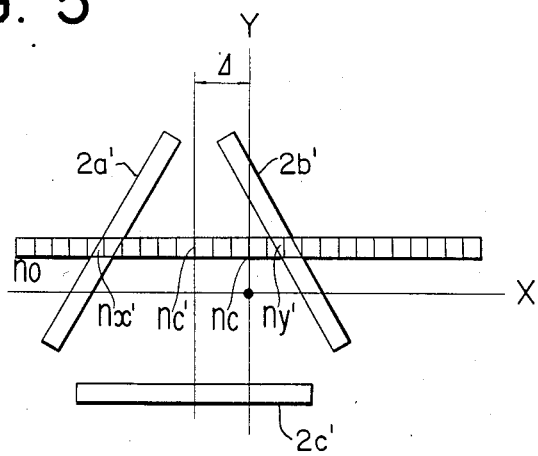

Description will now be made of cases where alignment of the eye to be examined and the present apparatus has not been properly effected. A first case is that where deviation occurs in the horizontal direction. If a deviation of $\Delta$ occurs as shown in FIG. 5, the output of the line sensor has its peaks deviated to $n_{x'}$ and $n_{y'}$ and $d' = n_{y'} - n_{x'}$ remains unchanged. If the mid-point between $n_{x'}$ and $n_{y'}$ is $n_{c'}$, $n_{c'} - n_{x'} = n_{y'} - n_{c'}$ and $n_c - n_{c'} = \Delta$.

Figure 6:
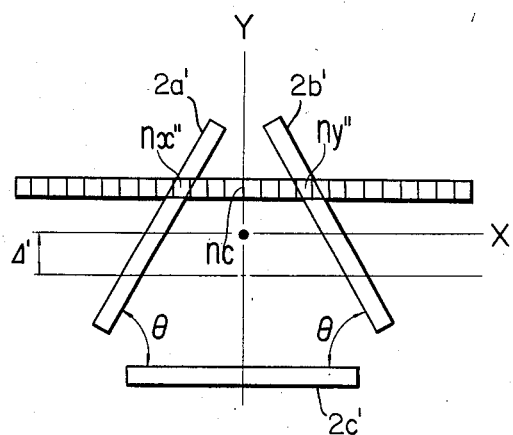

Second, a case where deviation has occurred in the vertical direction is shown in FIG. 6. If a deviation of $\Delta'$ occurs, the output of the line sensor has its peaks deviated to $n_{x''}$ and $n_{y''}$ and the interval $d'' = n_{y''} - n_{x''}$ therebetween increases or decreases relative to the interval $d = n_y - n_x$ when proper alignment has been achieved and therefore, it is compared with the reference value d stored in the ROM, whereby the deviation is detected. The amount of deviation $\Delta'$ can be calculated as $$\Delta = (d - d''/2) \cdot \tan \theta$$

if the angle formed between the corneal reflection images 2a', 2c' and 2b', 2c' is $\theta$.

Figure 8:
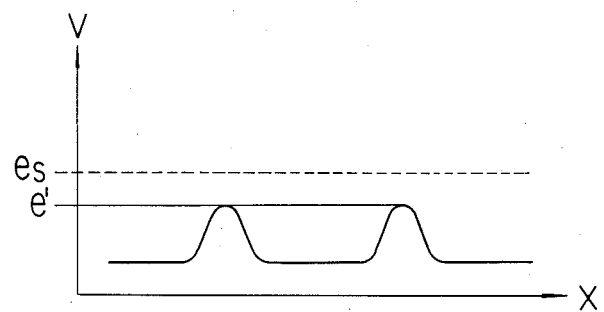

Third, where deviation has occurred in the longitudinal direction (the direction of the optic axis), the corneal reflection images blur on the line sensor and therefore, the output of the line sensor assumes a blunted waveform in which the peak level e' is low as shown in FIG. 8.

In the manner described above, the amounts of deviation of alignment in the three-dimensional directions may be detected. If the allowable ranges of the horizontal deviation $\Delta$ and the vertical deviation $\Delta'$ are previously stored in a memory and the allowable value of the peak level reduction is determined to be $e_s$ resulting from longitudinal deviation, when measurement has been effected in an alignment state in which the allowable ranges have been exceeded, a display device 29 is caused to display a warning, thereby urging a re-measurement.

Turning back to FIG. 1, a signal control circuit 30 will be described hereinafter. The output of the line sensor 18 is amplified by an amplifier 19, is converted into a digital signal by an A/D converter 20 and is transferred to RAM 24 via the bus line 21 of a microcomputer. Reference numeral 22 designates the microcomputer MPU and reference numeral 23 denotes a ROM which drives a line sensor control circuit 26 through an interface 25. Reference numeral 27 designates a letter signal generator, and reference numeral 28 denotes a mixing circuit for mixing video signals and letter signals.

When the eye to be examined is measured by the present apparatus, part of the measuring light is reflected by the cornea of the eye, that corneal reflection image is projected onto the line sensor 18, and the light and dark portion of the image are accumulated in the sensor 18. Subsequently, a sensor read-out signal is applied to the sensor control circuit 26, and an analog signal corresponding to the light and dark portions accumulated in the sensor 18 is A/D-converted and stored in the RAM 24. MPU 22 reads out the content of the RAM 24 and calculates what position on the sensor 18 is bright, and also calculates the level of the brightness. The details of the detection of alignment deviations are as previously described. That is, the address and level of brightness of the corneal reflection image on the sensor 18 are compared with the reference value stored in the ROM 23, whereby the amounts and directions of deviation of alignment in the vertical, horizontal and longitudinal directions can be calculated. When measurement has been effected in the state in which the amount of deviation in each direction has exceeded the allowable value, the display device 29 is caused to display the measurement data and display a warning to the effect that the alignment has no been proper. That is, letters or symbols are generated by the letter generator 27 and the letters or symbols are displayed on a part of the video image of the front eye part by the mixing circuit 28. When the alignment deviation is great and the reliability of the measured value has been remarkably reduced, the measurement data is not displayed but an instruction for re-measurement is displayed. For example, the instruction may be: "Longitudinal alignment has been deviated. Align properly once again and effect re-measurement.

Alternatively, as an alignment index, use may be made of 100 for the case where proper alignment has been effected, and the amounts of deviation in the respective directions may be added up and applied to a predetermined formula, whereby 85 or 90 may be displayed. When the index is 70 or less, it may be designated as a case which requires re-measurement.

Figure 9:
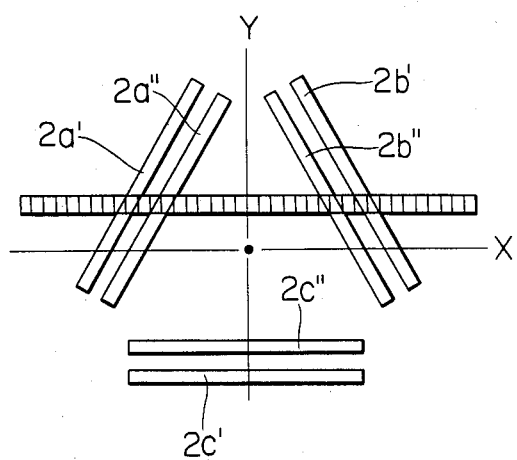
FIG. 9 is a plan view showing the positional relation between a line sensor in another embodiment and the corneal reflection images of a projection chart.
Figure 10:
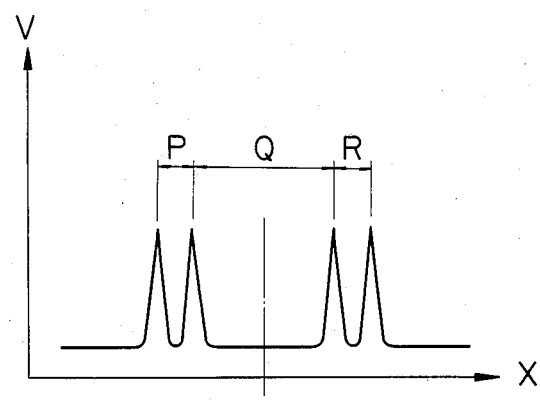
FIG. 10 shows the output waveform of the line sensor of the embodiment shown in FIG. 9.

FIG. 9 shows another embodiment which is similar in general construction to the first embodiment except for the pattern of the slits of the chart 2. In this embodiment, two slits are disposed in each direction and corneal reflection images 2a', 2a'' and 2b', 2b'' are formed on the line sensor. The output of the line sensor in this state is shown in FIG. 10.

The curvature of the cornea will now be considered. The curvature of the cornea differs from person to person and in many eyes to be examined, it is about R 7.6 mm, but it is greater or smaller in some eyes. In the first embodiment, if the curvature of the cornea varies, the imaging magnifications of the corneal reflection images 2a' and 2b' also vary though slightly, and the interval $d = n_y - n_x$ calculated from the output of the line sensor also varies. In many eyes to be examined, this variation is not so great that it affects the detection of alignment deviation, and the present embodiment can cope with eyes to be examined having curvatures of cornea greater or smaller than the normal curvature of cornea. That is, if the curvature of cornea of the eye to be examined varies, the interval Q varies in FIG. 10 while, at the same time, P and R also vary. When alignment is proper, P=R. Generally, there is established a predetermined relation between the curvature of cornea and (P/Q) or (P+Q+R/Q) and therefore, it is possible to effect correction by using this even when the radius of curvature of the cornea differs greatly from the standard (about 7.6 mm).

Figure 11:
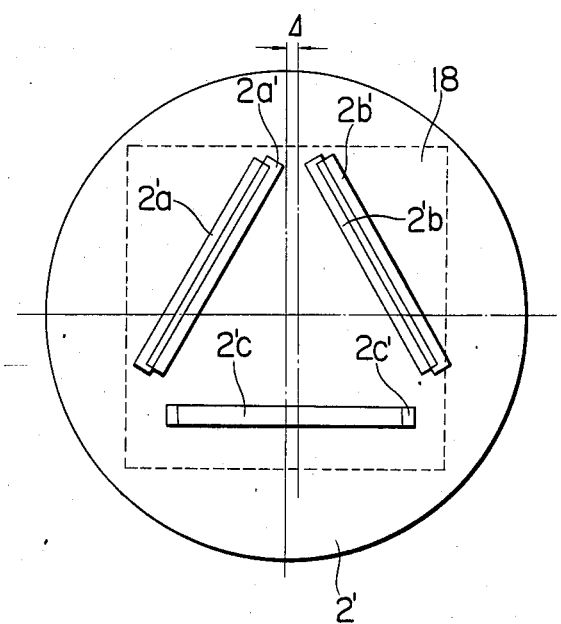
FIG. 11 is a plan view showing the positional relation between a light-receiving element in still another embodiment and the corneal reflection images of a projection chart.

FIG. 11 shows still another embodiment. A chart 2' identical or similar in shape to the chart 2 in FIG. 2 is disposed on a light-receiving element 18. The light-receiving element 18 is a single element such as a photodiode and the light-receiving surface thereof covers the slits 2'a, 2'b and 2'c of the chart 2'. If alignment deviates by Δ, the corneal reflection images 2a', 2b' and 2c' will deviate from the slits 2'a, 2'b and 2'c and the output of the light-receiving element 18 will be reduced. Also, if alignment deviates in the longitudinal direction, each corneal reflection image will blur and again the output of the light-receiving element will be reduced. That is, the output of the light-receiving element becomes maximum when alignments in all of the horizontal, vertical and longitudinal directions have been effected properly. Accordingly, a warning representing unsatisfactory alignment can be put out when the output of the light-receiving element has become less than a certain level. In this embodiment, although the direction and amounts of deviation cannot be detected, there is merit in that the apparatus can be made inexpensively and with a simple construction.

Further, if, although not shown, as an improvement over the present embodiment, three light-receiving elements 18a, 18b and 18c identical or similar in construction are disposed correspondingly to the slits 2'a, 2'b and 2'c, respectively, it will also become possible to detect the directions of deviation.

Thus, the present apparatus capable of determining the alignment accuracy has the following advantages:

1. It effects the determination of the alignment accuracy by the eye measuring light flux and therefore, as compared with an apparatus provided with a separate projection optical system for determining the alignment accuracy, it suffers from no deviation of the projected light flux and can be high in accuracy. Also, the measurement data provides material for directly judging in what position of the eye to be examined the measurement hs been carried out, and can be used for the judgment of propriety, the obtainment of a reliability coefficient, the correction of error, etc.

2. Since the determination is effected by the use of the information at the moment when actual measurement has been effected, it is possible to effect error-free determination even for quick movement of the eye.

3. The fact that determination of the vertical, horizontal and longitudinal directions can be achieved by a single line sensor leads to the provision of a simple apparatus.

What we claim is:

1. An ophthalmic instrument, comprising:
    an objective lens;
    means for projecting an eye-measuring target mark at the position substantially conjugate with the fundus of an eye to be examined through said objective lens onto the fundus of the eye to be examined;
    first and second beam splitting means each for splitting a light beam of the target mark and each being disposed to the side of said objective lens opposite to the side thereof on which the eye to be examined is disposed;
    a first detecting system for measuring predetermined information about a refractive power of the eye by projecting the light of said target mark reflected at the fundus of the eye onto a first detecting device through said objective lens, said first detecting device being provided at the position substantially conjugate with the fundus of the eye in a branched optical path formed by said first beam splitting means; and
    a second detecting system, including a second detecting device, for detecting the state of alignment between the eye to be examined and said ophthalmic instrument by projecting the light of said target mark reflected by the cornea of the eye onto said second detecting device through said objective lens, said second detecting device being provided at the position substantially conjugate with the corneal reflection image of said target mark in a branched optical path formed by said second beam splitting means.

2. An ophthalmic instrument according to claim 1, wherein said means for projecting said eye-measuring target mark projects a mark having at least two slit-like patterns and at least two of said slit-like patterns make an angle with respect to each other.

3. An ophthalmic instrument according to claim 2, wherein said second detecting device includes a plurality of sensors disposed in a line so that said line of sensors is crossed by the images of said slit-like patterns reflected by the cornea of the eye and the angles formed by said images of said patterns with said line of sensors are equal to each other when the state of alignment between the eye and said ophthalmic instrument is proper.

4. An ophthalmic instrument according to claim 3, further comprising a control operational circuit for detecting from the outputs of said line of sensors the addresses of said sensors in said line representing the positions at which the images of said slit-like patterns are formed and the levels of brightness of the pattern images.

5. An ophthalmic instrument according to claim 4, wherein said control operational circuit further comprises means for storing a reference value for the addresses of the images of said slit-like patterns and a reference value for the levels of brightness representing the proper alignment state.

6. An ophthalmic instrument according to claim 1, further comprising a television camera for visualizing a front-eye-part-illuminating target mark light flux and an aligning target mark light flux.

7. An ophthalmic instrument according to claim 1, wherein said means for projecting said eye-measuring target mark projects a mark having at least two sets of slit-like patterns, said patterns in each set being parallel to each other.

8. An ophthalmic instrument according to claim 2, wherein said second detecting system includes means defining opening portions each parallel to one said slit-like pattern and at least one of identical and similar in shape to each other.

9. An ophthalmic instrument according to claim 1, further comprising means for displaying a warning when eye measurement is effected by said first detecting means in a state of alignment detected by said second detecting system that deviates from the proper state of alignment by more than an allowable amount.

10. An ophthalmic instrument according to claim 1, wherein said means for projecting said eye-measuring target mark projects a mark having slit-like patterns extending in at least three directions.

* * * * *